United States Patent [19]

Taylor et al.

[11] Patent Number: 4,895,946

[45] Date of Patent: Jan. 23, 1990

[54] PROCESS FOR THE PREPARATION OF FUSED PYRIDINE COMPOUNDS

[75] Inventors: Edward C. Taylor, Princeton, N.J.; Philip M. Harrington, Plainwell, Mich.

[73] Assignee: The Trustees of Princeton University, Princeton, N.J.

[21] Appl. No.: 186,015

[22] Filed: Apr. 25, 1988

Related U.S. Application Data

[63] Continuation-in-part of Ser. No. 114,030, Oct. 26, 1987, abandoned.

[51] Int. Cl.$^4$ ............................................. C07D 471/04
[52] U.S. Cl. .................................... 544/279; 558/406; 560/51; 560/64
[58] Field of Search ................ 544/279, 257, 258, 259

[56] References Cited

U.S. PATENT DOCUMENTS 3,288,792 11/1986 Hitchings et al. ................... 544/279
4,372,957 2/1983 Duch et al. ........................... 514/258

OTHER PUBLICATIONS

Advanced Organic Chemistry by Jerry March (2nd Ed.), pp. 684–685, (1977).

*Primary Examiner*—Mukund J. Shah
*Assistant Examiner*—Emily Bernhardt
*Attorney, Agent, or Firm*—Mathews, Woodbridge, Goebel, Pugh & Collins

[57] ABSTRACT

Pyrido[2,3-d]pyrimidine compounds are prepared through the reaction of 2,4-diamino-6(1H)-pyrimidone and an activated derivative of a dialdehyde. A typical embodiment utilizes the dinitrile.

8 Claims, No Drawings

PROCESS FOR THE PREPARATION OF FUSED PYRIDINE COMPOUNDS

This invention pertains to a process for the preparation of known therapeutic agents, to chemical intermediates useful therein, and to novel therapeutic agents heretofore not available by known methods.

BACKGROUND OF THE INVENTION

Compounds of the formula:

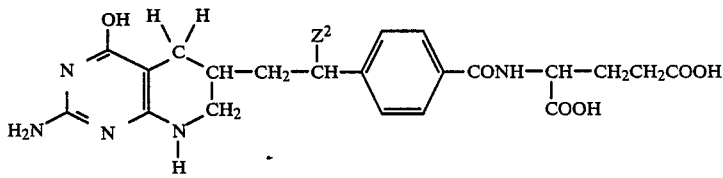

in which $Z^2$ is hydrogen, methyl, or ethyl are broad spectrum antineoplastic agents. See U.S. Pat. No. 4,684,653. These compounds, of which N-(4-[2-(2-amino-4-hydroxy-5,6,7,8-tetrahydropyrido[2,3-d]pyrimidin-6-yl)ethyl]benzoyl)-L-glutamic acid is representative, have been prepared previously through a lengthy synthesis in which a 2-(protected amino)-4-hydroxy-6-[2-(4-carboxyphenyl)ethyl]pyrido[2,3-d]pyrimidine is coupled with a diester of L-glutamic acid utilizing peptide condensation techniques. The resultant dialkyl N-(4-[2-(2-protected amino-4-hydroxypyrido[2,3-d]-pyrimidin-6-yl)ethenyl]benzoyl)-L-glutamate is then hydrogenated, following which the protecting groups are removed. By reason of the ethenyl intermediate, the process is limited to the preparation of compounds having at least two carbon atoms in the bridge between the tetraydropyridine ring and the phenyl ring.

DETAILED DESCRIPTION

The present invention provides a simplified process for the preparation of important intermediates useful in the synthesis of the foregoing compounds. In particular, this process leads to intermediates of the formula:

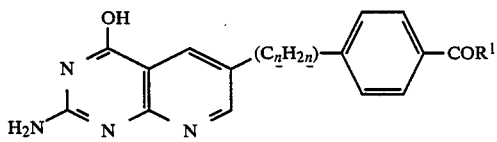

wherein:
$R^1$ is —NHCH(COOR$^2$)CH$_2$CH$_2$COOR$^3$, or OR$^2$, in which each of $R^2$ and $R^3$ is hydrogen or a carboxylic acid protecting group; and
n has a value of from 1 to 3.

In addition, the process permits preparation of N-[4-(2-amino-4-hydroxy-5,6,7,8-tetrahydropyrido[2,3-d]-pyrimidin-6-ylmethyl)benzoyl]-L-glutamic acid and N-(4-[3-(2-amino-4-hydroxy-5,6,7,8-tetraydropyrido-[2,3,-d]pyrimidin-6-yl)propyl]benzoyl)-L-glutamic acid, novel compounds which heretofore were not available using known synthetic methods.

According to the present process, 2,4-diamino-6(1H)-pyrimidinone is allowed to react with a compound of the formula:

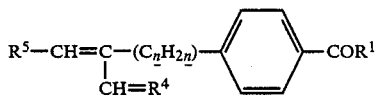

in which
$R^1$ and n are as herein defined;
$R^4$ is =O or

$R^5$ is —OR$^8$ or

each of $R^6$ and $R^7$, independently of the other, is a strong electron withdrawing group; and
each of $R^8$ and $R^9$, independently of the other, is hydrogen or alkyl of 1 to 6 carbon atoms, or $R^8$ and $R^9$, together with the nitrogen atom to which they are attached, are pyrrolidino, morpholino, or piperidino.

The reaction can be conducted simply by heating the reagents at reflux in a suitable solvent such as acetic acid and requires no other reagents nor catalyst.

When $R^5$ is OR$^8$, $R^8$ is hydrogen, and $R^4$ is =O, the intermediate of Formula II is a tautomer (with respect to $R^8$) of a dialdehyde. Conceptually, therefore, the process may be viewed in this, the simplest case, as the reaction between 2,4-diamino-6(1H)-pyrimidone and the dialdehyde:

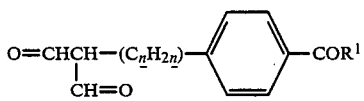

It is preferable, however, to employ an activated form of the dialdehyde of Formula IIA, namely a compound of Formula II in which $R^4$ is

Each of $R^6$ and $R^7$ is a strong electron withdrawing group such as cyano, nitro, formyl, carboxy, —S—R$^{10}$, —SOR$^{10}$, —SO$_2$R$^{10}$, —COR$^{10}$, or —COOR$^{10}$ in which $R^{10}$ is an inert aliphatic, cycloaliphatic or aromatic monovalent hydrocarbon group. Alternatively, $R^{10}$ can include a single divalent group bound to both $R^6$ and $R^7$, $R^4$ thus can be 4,4-dimethyl-2,6-dioxocyclohex-1,1-ylidene, dicyanomethylidene, carbethoxy, cyanomethylidene, bis(carbethoxy)methylidene, nitrocyanomethylidene, and the like. Since such $R^4$ groups merely provide activation, the precise nature of $R^6$ and $R^7$ is unimportant and they will be exemplified herein by each of $R^6$ and $R^7$ being cyano.

When $R^5$ is $-OR^8$, $R^8$ can be hydrogen or an alkyl group, in which case the composite $R^8-O-CH=$ may be viewed as an enol ether. Alternatively, $R^5$ can be an amino group, a monoalkylamino group, a dialkylamino group, or a nitrogen containing heterocyclic group such as pyrrolidino, morpholino, piperidino, homopiperidino, and the like.

The subscript n can have a value of 1,2 or 3, thus including methylene, 1,1-ethylidene, 1,2-ethylene, 1,1-propylidene, 1,2-propylene, 2,3-propylene, and 1,3-propylene. It will be appreciated that 1,2-propylene in the present context denotes the compound of Formula I in which the secondary carbon atom in the 2-position of the propylene chain is adjacent to the depicted pyridine ring while 2,3-propylene denotes the separate compound in which the secondary carbon atom of the propylene is adjacent to the depicted phenyl ring.

$R^1$ can be $OR^2$ in which $R^2$ is hydrogen or a carboxylic acid protecting group; i.e., the compounds are 4-substituted benzoic derivatives or protected derivatives thereof.

When $R^1$ is $-OH$; i.e., a benzoic acid derivative, the compound can be coupled with a protected derivative L-glutamic acid as described for example in U.S. Pat. No. 4,684,653 to yield a protected N-(4-[(2-amino-4-hydroxypyrido[2,3-d]pyrimidin-6-yl)alkyl]benzoyl)-L-glutamic acid derivative. This can then be hydrogenated to yield the corresponding 5,6,7,8-tetrahydro compound in the manner therein described.

Alternatively, if $R^1$ in Formula I is the residue of L-glutamic acid, $-NHCH(COOR^2)CH_2CH_2COOR^3$, the product of the present process, after removal of any protecting groups embodied by $R^2$ and $R^3$, is an N-(4-[(2-amino-4-hydroxypyrido[2,3-d]pyrimidin-6-yl)alkyl]-benzoyl)-L-glutamic acid, which can be hydrogenated as previously described.

When n is 2 in Formula (I), the products correspond to the compounds of U.S. Pat. No. 4,684,653. The methods described in that patent, however, are inherently limited to a two carbon bridge, optionally containing a branched methyl group. By reason of the present process it is possible to prepare the corresponding compound wherein there is a single carbon bridge, optionally carrying a branched methyl group as a substituent (ethylidene) or ethyl group as a substituent (propylidene). This process also permits preparation of the compounds in which there is a trimethylene bridge. These derivatives are novel antimetabolites not previously available by known synthetic methods.

Among the novel intermediates thus provided are compounds of the formula:

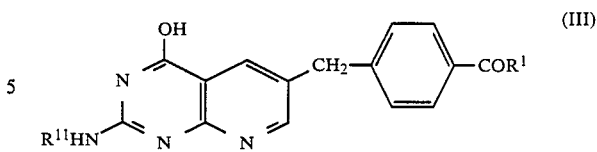

wherein:
$R^1$ is $-NHCH(COOR^2)CH_2CH_2COOR^3$, or $OR^2$ in which $R^2$ and $R^3$ is hydrogen or a carboxylic acid protecting group; and
$R^{11}$ is hydrogen or an amino protecting group:

and a compound of the formula:

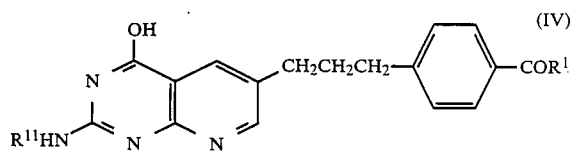

wherein:
$R^1$ is $-NHCH(COOR^2)CH_2CH_2COOR^3$, or $OR^2$ in which $R^2$ and $R^3$ is hydrogen or a carboxylic acid protecting group; and
$R^{11}$ is hydrogen or an amino protecting group.

Catalytic hydrogenation of a compound of Formula I yields the corresponding 2-amino (or 2-protected amino)-4-hydroxy-6-substituted-5,6,7,8-tetrahydropyrido[2,3-d]-pyrimidine:

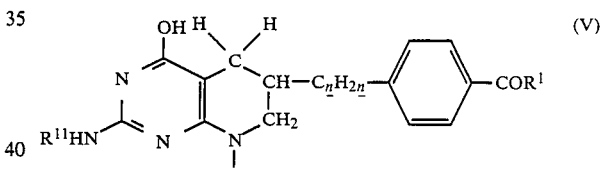

in which $R^1$ is $-NHCH(COOR^2)CH_2CH_2COOR^3$, or $OR^2$ in which $R^2$ and $R^3$ is hydrogen or a carboxylic acid protecting group; and $R^{11}$ is hydrogen or an amino protecting group.

The hydrogenation is conducted in an acidic medium in the presence of a noble metal catalyst such as platinum, ruthenium or rhodium, including the oxides thereof and the supported forms thereof. The preferred catalyst is platinum oxide. Conditions of time, temperature, and pressure are selected so that reduction of the pyridine ring is achieved without involvement of the pyrimidine ring. With platinum oxide, for example, the desired product is obtained in about 15 minutes utilizing ambient temperatures and a hydrogen pressure of 50 to 60 psi.

Protecting groups encompassed by $R^2$ and $R^3$ and reactions for their removal are described, for example, in "Protective Groups in Organic Chemistry", Plenum Press, London and New York (1973); Greene, "Protective Groups in Organic Synthesis", Wiley, New York (1981); "The Peptides", Vol. I, Schröder and Lubke, Academic Press, London and New York (1965); in "Methoden der organischen Chemie", Houben-Weyl, 4th Edition, Vol. 15/I, Georg Thieme Verlag, Stuttgart (1974).

Carboxylic acid protecting groups can be, for example, esters derived from lower alkanols of from 1 to 6 carbon atoms, including those branched in the 1-position and those which are substituted with one or more aromatic groups such as phenyl, or with halo or alkoxy; e.g., methyl, ethyl, t-butyl, benzyl, 4-nitrobenzyl, diphenylmethyl, methoxymethyl, and the like esters. Silyl esters such as trimethylsilyl also can be employed.

The hydrolysis of such protecting groups is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the product is initially formed as the dicationic glutamate salt and can be readily precipitated by adjustment of pH, as through acidification with, for example, acetic acid. The resulting products generally are high melting crystalline or microcrystalline solids.

Two chiral centers are present in the final molecule of Formula V in which $R^1$ is —NHCH($COOR^2$)$CH_2CH_2$($COOR^3$): the carbon atom in the 6-position of the tetraydropyrido[2,3,-d]pyrimidine ring and the alpha carbon atom in the glutamic acid group. Of the theoretical four forms of the compound, the use of an L-glutamic acid reagent in the preparation of a compound of Formula I or II reduces the possibilities to two. Both remaining chiral forms, however, are generated during the subsequent hydrogenation to a compound of Formula V and consequently, upon removal of any protecting groups, the desired compound is produced as a mixture of the (S,S) and (R,S) diastereomers. These can be represented for the compound of Formula V in which $R^1$ is —NHCH(COOH)$CH_2CH_2$COOH and $R^{11}$ is hydrogen as follows:

(S,S):

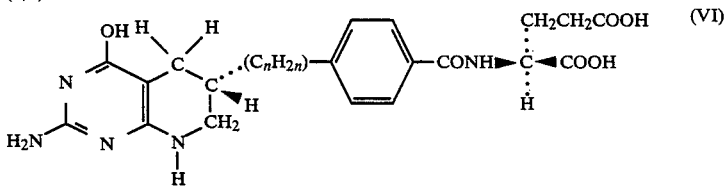

(VI)

(R,S):

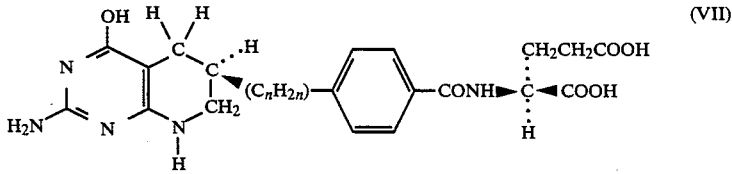

(VII)

These diastereomers can be separated mechanically, as by chromatography, so that each is in a form substantially free of the other; i.e., having an optical purity of >95%. Alternatively, a mixture of diastereoisomeric compounds is treated with a chiral acid operable to form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cation of the salt can be performed as a discrete step before or after the removal of the protecting groups, or concomitantly with the removal when such groups are susceptible to removal under basic conditions; i.e., basic hydrolysis.

Suitable chiral acids include the individual enantiomers of 10-camphorsulfonic acid, camphoric acid, alpha bromocamphoric acid, menthoxyacetic acid, tartaric acid, diacetyltartaric acid, malic acid, pyrrolidone-5-carboxylic acid, and the like.

The invention includes the pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like.

The compounds of Formula V in which $R^1$ is —NHCH($COOR^2$)$CH_2CH_2COOR^3$ have an effect on one or more enzymes which utilize folic acid, and in particular metabolic derivatives of folic acid, as a substrate. They can be used, alone or in combination, to treat neoplasms which in the past have been treated with methotrexate, including choriocarcinoma, leukemia, adenocarcinoma of the female breast, epidermid cancers of the head and neck, squamous or small-cell lung cancer, and various lymphosarcomas. The compounds can also be used to treat mycosis fungoides, psoriasis and arthritis. The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intraarterial. In general, the compounds are administered in much the same fashion as methotrexate, but because of a different mode of action, can be administered in higher dosages than those usually employed with methotrexate. Dosage regimens must be titrated to the particular neoplasm, the condition of the patient, and the response but generally doses will be from about 10 to about 100 mg/day for 5–10 days or single daily administration of 250–500 mg, repeated periodically; e.g., every 14 days. Oral dosage forms include tablets and capsules containing from 1–10 mg of drug per unit dosage. Isotonic saline solutions containing 20–100 mg/ml can be used for parenteral administration.

The following examples will serve to further illustrate the invention.

EXAMPLE 1

Two grams of methyl 4-(3-ethoxymethylene-5,5-dicyanopent-4-en-1-yl)benzoate, 0.93 g of 2,4-diamino-6(1H)-pyrimidone, and 30 mL of acetic acid are heated at reflux with stirring for 4 hours. The reaction mixture is allowed to cool to room temperature and the solid which forms is collected by filtration, washed with water and diethyl ether and dried to yield methyl 4-[2-(2-amino-4-hydroxypyrido[2,3-d]pyrimidin6-yl)-ethyl]-benzoate, m.p.>300° C.; IR (KBr) $\nu_{max}$ 3320, 2950, 1720, 1657, 1626, 1610, 1455, 1280, 1251, 1148, 1109, and 834 cm$^{-1}$; $^1$H NMR (dTFA, d$^6$DMSO) delta 8.38 (s, 1H (7)—H), 7.99 (s, 1H, (5)—H), 7.55 (d, J=8.0 Hz, 2H, Ar), 6.87 (s, 1H (3)—H), 6.82 (d, J=8.0 Hz, 2H, Ar), 3.56 (s, 3H, —CH$_3$), 2.77–281 (m, 2H, (6)—CH$_2$—), 2.67–2.73 (m, 2H, benzyl).

Anal. Calcd. for C$_{17}$H$_{16}$N$_4$O$_3$: C, 62.95; H, 4.97; N, 17.27. Found: C, 62.65; H, 5.03; N, 17.06.

EXAMPLE 2

By substituting an equivalent amount of methyl 4-(4-ethoxymethylene-6,6-dicyanohex-5-en-1-yl)benzoate for methyl 4-(3-ethoxymethylene-5,5-dicyanopent-4-en-1-yl)benzoate in the procedure of Example 1, there is obtained methyl 4-[3-(2-amino-4-hydroxypyrido[2,3-d]pyrimidin-6-yl)propyl]benzoate, m.p. >250° C.; IR (KBr) $\nu_{max}$ 3220, 3050, 2920, 2820, 1700, 1662, 1589, 1551, 1472, 1398, 1272, 1168, 1094, 1011, 850, 800, and 740 cm$^{-1}$; $^1$H NMR (dTFA, d$^6$DMSO) delta 8.48 (s, 1H (7)—H), 8.16 (s, 1H, (5)—H), 7.53 (d, J=8.2 Hz, Ar), 6.87 (d, J=8.2 Hz, 2H, Ar), 1H, 3.56 (s, 3H, —CH$_3$), 2.38–2.49 (m, 4H, benzyl, (6)—CH$_2$—), 1.65–1.70 (m, 2H, 2° aliphatic).

Anal. Calcd. for C$_{18}$H$_{18}$N$_4$O$_3$: C, 63.89; H, 5.36; N, 16.56. Found: C, 64.15; H, 5.60; N, 16.79.

EXAMPLE 3

The starting materials for Examples 2 and 3 can be obtained according to the following representative procedures:

A. A mixture of 3.36 g (1.0 eq) of 4-(4-carbomethoxyphenyl)butanal, 1.29 g (1.2 eq) of malononitrile, 0.05 g of D,L-alanine, 1 mL of glacial acetic acid, and 60 mL of benzene is refluxed with azeotropic removal of water. After 3 hours, about 85% of the theoretical amount of water should be formed and removed. The mixture then is cooled to room temperature and poured into water. The aqueous layer is extracted twice with benzene and the combined organic layers are dried over sodium sulfate, filtered and concentrated under reduced pressure. Chromatography with 1:1 ethyl acetate:hexanes and concentration of the eluant yield methyl 4-(5,5-dicyanopentyl) benzoate as an oil. IR (film) $\nu_{max}$ 2240, 1718, 1615, 1280, and 1110 cm$^{-1}$; $^1$H NMR (CDCl$_3$) delta 7.99 (d, J=8.1 Hz, 2H, Ar), 7.24–7.29 (m, 3H, Ar, vinyl), 3.90 (s, 3H, —CH$_3$), 2.79 (t, J=7.4 Hz, 2H, benzyl), 2.60–2.64 (m, 2H, —CH$_2$C═C), 1.94–1.97 (m, 2H, —CH$_2$—).

Similarly prepared is methyl 4-(6,6-dicyanohex-5-en-1-yl)benzoate, $^1$H NMR (CDCl$_3$) delta 7.98 (d, J=8.2 Hz, 2H, Ar), 7.31 (t, J=8.0 Hz, 1H, vinyl), 7.25 (d, J=8.2 Hz, 2H, Ar), 3.91 (s, 3H, —CH$_3$), 2.72 (t, J=7.4, Hz, 2H, benzyl), 2.59–2.65 (m, 2H, —CH$_2$C═C), 1.56–1.79 (m, 6H, 2° aliphatic).

These products will show decomposition upon standing at room temperature and should be used promptly in the following procedure.

B. A mixture of 8.23 g (30.7 mmol) of methyl 4-(5,5-dicyanopent-4-en-1-yl)benzoate, 76.5 mL (461 mmol) of triethyl orthoformate, 86.8 mL (922 mmol) of acetic anhydride, and 0.10 of zinc chloride as catalyst is refluxed with stirring and the exclusion of moisture at 145° C. for 18 hours. The mixture is cooled and the volatiles removed by heating at 100° C. An additional 51.0 mL (307 mmol) of triethyl orthoformate and 57.9 mL (614 mmol) of acetic anhydride are added and this mixture is heated at reflux with stirring and the exclusion of moisture at 150° C. for 12 hours.

The reaction mixture is cooled, poured into water and extracted with chloroform. The combined organic extracts are dried, filtered, and concentrated and again filtered through silica gel. Ethanol is added to the filtrate and this mixture is concentrated to yield methyl 4-(3-ethoxymethylidene-5,5-dicyanopent-4-en-1-yl)benzoate, m.p. 136°–137° C.; IR (KBr) $\nu_{max}$ 2900, 2210, 1700, 1596, 1560, 1437, 1280, 1208, 1006, 879, and 763 cm$^{-1}$; $^1$H NMR (CDCl$_3$) delta 7.96 (d, J=8.2 Hz, 2H, Ar), 7.33 (d, J=8.2 Hz, 2H, Ar), 7.06 (s, 1H, —CH═C(CN)$_2$), 6.95 (s, 1H, vinyl), 4.10 (q, J=7.1 Hz, 2H, —OCH$_2$—), 3.92 (s, 3H, —CH$_3$), 2.88 (m, 4H, ArCH$_2$—CH$_2$—), 1.30 (t, J=7.2 Hz, 3H, —CH$_3$—CH$_2$O).

Anal. Calcd. for C$_{18}$H$_{18}$N$_2$O$_3$: C, 69.66; H, 5.85; N, 9.03. Found: C, 69.47; H, 5.68; N, 8.86.

Similarly prepared is methyl 4-(4-ethoxymethylidene-6,6-dicyanohex-5-en-1-yl)benzoate, m.p. 81.5°–82.5° C.; IR (KBr) $\nu_{max}$ 2965, 2930, 2905, 2840, 2195, 1696, 1590, 1555, 1418, 1379, 1350, 1273, 1214, 1098, 1009, 953, 877, 756, and 696 cm$^{-1}$; $^1$H NMR (CDCl$_3$) delta 7.96 (d, J=8.2 Hz, 2H, Ar), 7.28 (d, J=8.2 Hz, 2H, Ar), 7.04 (s, 1H, —CH═C(CN)$_2$), 6.97 (s, 1H, vinyl), 4.20 (q, J=7.2 Hz, 2H, —OCH$_2$—), 3.92 (s, 3H, —CH$_3$), 2.76 (t, J=8.0 Hz, 2H, benzyl), 2.62 (t, J=7.9 Hz, 2H, ArCH$_2$CH$_2$), 1.76–1.84 (m, 2H, 2° aliphatic) 1.39 (t, J=7.0 Hz, 3H, —CH$_3$—CH$_2$O).

Anal. Calcd. for C$_{19}$H$_{20}$N$_2$O$_3$: C, 70.35; H, 6.21; N, 8.64. Found: C, 70.10; H, 6.34; N, 8.47.

EXAMPLE 4

The aldehyde starting materials utilized in Example 3 are known or can be prepared by known procedures from the corresponding alcohols through oxidation, of which the following procedures are typical.

A. To a mixture of 0.082 g (0.005 eq) of palladium chloride, and 0.244 g (0.01 eq) of triphenylphosphine, and 20.00 g (1.0 eq) of methyl 4-bromobenzoate in diethylamine which is stirred under nitrogen is added 0.178 g (0.01 eq) of copper (I) iodide and 6.52 g (1.0 eq) of 3-butyn-1-ol. The reaction mixture is stirred under nitrogen at room temperature (about 25° C.) for eighteen hours. Diethylamine is then removed under reduced pressure, water is added, and the mixture extracted with benzene. The benzene extracts are filtered through silica to remove the metal residue and the filtrate concentrated under reduced pressure to yield methyl 4-(4-hydroxybut-1-yl)benzoate. Recrystallization from a mixture of benzene and hexane yields pure material in 75.8% yield, m.p. 95.5°–96.0° C.; IR (KBr) $\nu_{max}$ 3310, 2955, 1718, 1604, 1433, 1275, 1177, 1108, 1040, 955, 852, and 769 cm$^{-1}$; $^1$H NMR (CDCl$_3$) delta 7.98 (d, J=8.3 Hz, 2H, Ar), 7.49 (d, J=8.3 Hz, 2H, Ar), 3.93 (s, 3H, —CH$_3$), 3.87 (m, 2H, —CH$_2$OH), 2.74 (t, J=6.2 Hz, 2H, —yl—CH$_2$—), 1.88 (m, 1H, —OH).

Anal. Calcd. for C$_{12}$H$_{12}$O$_3$: C, 70.57; H, 5.92. Found: C, 70.36; H, 5.68.

By substituting 4-pentyn-1-ol for 3-butyn-1-ol, for 3-butyn-1-ol, there is similarly obtained methyl 4-(5-hydroxypent-1-yn-1-yl)benzoate in 83% yield, m.p. 68.5°–69.5° C.; IR (KBr) $\nu_{max}$ 3360, 2955, 2855, 2220, 1720, 1604, 1431, 1405, 1307, 1272, 1193, 1172, 1112, 1063, 1017, 963, 904, 859, 769, and 696 cm$^{-1}$; $^1$H NMR (CDCl$_3$) delta 7.96 (d, J=8.3 Hz, 2H, Ar), 7.45 (d, J=8.3 Hz, 2H, Ar), 3.92 (s, 3H, —CH$_3$), 3.80–3.87 (m, 2H, —CH$_2$OH), 2.58 (t, J=7.0 Hz, 2H, yl—CH$_2$), 1.63 (bs, 1H, —OH).

Anal. Calcd. for C$_{13}$H$_{14}$O$_3$: C, 71.54; H, 6.47. Found: C, 71.26; H, 6.38.

B. A mixture of 2.55 g of methyl 4-(4-hydrox-but-1-yn-1-yl)benzoate in 200 mL of ethanol is hydrogenated at 50 psi of hydrogen for 12 hours in the presence of 0.26 g (10% weight equivalent) of 5% palladium on charcoal. The reaction mixture is filtered through a silica gel pad, which is washed with ethanol, and concentrated to yield methyl 4-(4-hydroxybutyl)benzoate as an oil. IR (film) $\nu_{max}$ 3390, 2965, 2920, 2850, 1705, 1605, 1568, 1520, 1500, 1410, 1387, 1362, 1308, 1286, 1250, 1160, 1055, 1013, 843, 755, and 695 cm$^{-1}$; $^1$H NMR (CDCl$_3$) delta 7.95 (d, J=8.1 Hz, 2H, Ar), 7.25 (d, J=8.1 Hz, 2H, Ar), 3.89 (s, 3H, —CH$_3$), 3.65 (t, J=6.3 Hz, 2H, —CH$_2$OH), 2.69 (t, J=7.5 Hz, 2H, benzyl), 1.66 (m, 4H, 2° aliphatic).

Anal. Calcd. for C$_{12}$H$_{16}$O$_3$: C, 69.21; H, 7.74. Found: C, 68.97; H, 7.92.

Similarly prepared is methyl 4-(5-hydroxypentyl)benzoate, IR (film) $\nu_{max}$ 3380, 2905, 2835, 1700, 1598, 1562, 1424, 1405, 1300, 1266, 1168, 1097, 1058, 1036, 1010, 953, 834, 747, and 692 cm$^{-1}$; $^1$H NMR (CDCl$_3$) delta 7.94 (d, J=8.1 Hz, 2H, Ar), 7.23 (d, J=8.1 Hz, 2H, Ar), 3.89 (s, 3H, —CH$_3$), 3.62 (t, J=6.5 Hz, 2H, —CH$_2$OH), 2.66 (t, J=7.7 Hz, 2H, benzyl), 1.86 (bs, 1H, OH), 1.53–1.71 (m, 4H, 2° aliphatic), 1.35–1.45 (m, 2H, 2° aliphatic).

Anal. Calcd. for C$_{13}$H$_{18}$O$_3$: C, 70.25; H, 8.16. Found: C, 70.05; H, 8.17.

C. To mixture of 4.19 g (1.5 eq) of pyridinium chlorochromate and 1.76 g (1.0 eq) of sodium acetate in 100 mL of dry methylene chloride are added, under nitrogen and with stirring, 2.70 g 1.0 eq) of methyl 4-(4-hydroxybutyl)benzoate in 50 mL of dry methylene chloride. The reaction mixture is stirred 12 hours, diluted with diethyl ether, and filtered. After concentration at reduced pressure, the residue is distilled under vacuum to yield 4-(4-carbomethoxyphenyl)-butanal as an oil, b.p. 131° C. at <1 torr; IR (film) $\nu_{max}$ 2950, 2720, 1722, 1612, 1285, and 1110 cm$^{-1}$; $^1$H NMR (CDCl$_3$) delta 9.77 (m, 1H, —CHO), 7.98 (d, J=9 Hz, 2H, Ar), 7.24 (d, J=8.2 Hz, 2H, Ar), 3.90 (s, 3H, —CH$_3$), 2.72 (t, 2H, benzyl), 2.47 (mm, 2H, —CH$_2$CHO), 1.95 (m, 2H, —CH$_2$).

Similarly prepared is 5-(4-carbomethoxyphenyl)pentanal, b.p. 133°–134° C. at <1 torr; IR (film) $\nu_{max}$ 2920, 2840, 2705, 1708, 1600, 1562, 1425, 1406, 1267, 1168, 1099, 1010, 952, 844, 749, and 692 cm$^{-1}$; $^1$H NMR (CDCl$_3$) delta 9.73 (t, J=1.9 Hz, CHO), 7.94 (d, J=8.2 Hz, 2H, Ar), 7.22 (d, J=8.2 Hz, 2H, Ar), 3.88 (s, 3H, —CH$_3$), 2.67 (t, J=6.9 Hz, 2H, benzyl), 2.41–2.47 (m, 2H, —CH$_2$CHO), 1.62–1.68 (m, 4H, 2° aliphatic).

EXAMPLE 5

A mixture of 0.46 g of methyl 4-[2-(2-amino-4-hydroxypyrido[2,3d]pyrimidin-6-yl]ethyl]benzoate and 30 mL of 1N sodium hydroxide is stirred at room temperature for 36 hours and then acidified with glacial acetic acid. The resulting suspension is centrifuged with fresh water several times and then combined with methanol. The water is removed azeotropically under reduced pressure to yield 4-[2-(2-amino-4-hydroxypyrido[2,3-d]-pyrimidin-6-yl)ethyl]benzoic acid, m.p. >300° C.; IR (KBr) $\nu_{max}$ 3220, 2855, 1680, 1607, 1483, 1398, 1253, 1179, 1016, and 812 cm$^{-1}$; $^1$H NMR (dTFA, d$^6$DMSO) delta 8.38 (s, 1H (7)—H), 8.02 (s, 1H, (5)—H), 7.62 (d, J=8.0 Hz, 2H, Ar), 6.87 (s, 1H, (3)—H), 6.82 (d, J=8.0 Hz, 2H, Ar), 2.79 (m, 2H, (6)—CH$_2$—), 2.70 (m, 2H, benzyl).

Similarly prepared is 4-[3-(2-amino-4-hydroxypyrido[2,3-d]pyrimidin-6-yl)propyl]benzoic acid, m.p. >300° C.; IR (KBr) $\nu_{max}$ 3200, 2900, 2830, 1560, 1410, 1235, 1032, 1000, 911, and 796 cm$^{-1}$; $^1$H NMR (dTFA), d$^6$DMSO) delta 8.52 (s, 2H (7)—H), (5)—H), 7.72 (d, J=8.1 Hz, 2H, Ar), 2.48–2.56 (m, 4H, benzyl, (6)—CH$_2$—), 1.76–1.83 (m, 2H, 2° aliphatic).

EXAMPLE 6

A mixture of 0.40 g (1.0 eq) of 4-[2-(2-amino-4-hydroxypyrido[2,3-d]pyrimidin-6-yl)ethyl]benzoic acid, 10 mL of pivalic anhydride, and 0.02 g (0.1 eq) of 4-(N,N-dimethylamino)pyridine is heated at reflux with stirring and under nitrogen for 6 hours. Fifty milliliters of diethyl ether are added and the solid collected by filtration. This is triturated with water and 1N solium hydroxide is added dropwise until a clear solution is obtained (in order to hydrolyse any mixed anhydride which is present). The mixture is then acidified with glacial acetic acid and the solid which forms is collected by filtration and washed sequentially with water, methanol, acetone, and diethyl ether. The solid which forms in the filtrate is collected by filtration and washed with diethyl ether to yield 4-[2-(2-pivaloyl-amino-4-hydroxypyrido[2,3-d]-pyrimidin-6-yl)ethyl]benzoic acid, m.p. >300° C.; IR (KBr) $\nu_{max}$ 3420, 3200, 2945, 1680, 1607, 1569, 1448, 1401, 1250, 1154, 1018and 812 cm$^{-1}$; $^1$H NMR (dTFA, CDCl$_3$) delta 9.03 (s, 1H (7)—H), 8.73 (s, 1H, (5)—H), 8.14 (d, J=8.2 Hz, 2H, Ar), 3.36 (t, J=7.4 Hz, 2H (6)—CH$_2$), 3.24 (t, J=7.2 Hz, 2H, benzyl), 1.46 (s, 9H, t-butyl).

HRMS Calcd. for C$_{21}$H$_{22}$N$_4$O$_4$(M$^+$): 394.4292. Found: 394.1649; other ions at m/e 350, 337, 319, 293, 259, 217, 201, 175, 133.

Similarly prepared is 4-[3-(2-pivaloylamino-4-hydroxypyrido[2,3-d]pyrimidin-6-yl)propyl]benzoic acid, m.p. 257°–258° C.; IR (KBr) $\nu_{max}$ 3160, 2945, 2910, 2840, 1670, 1605, 1549, 1440, 1388, 1302, 1233, 1138, 1092, 1008, 950, 801, and 749 cm$^{-1}$; $^1$H NMR (dTFA, d$^6$DMSO) delta 8.64 (s, 1H (7)—H), 8.27 (s, 1H, (5)—H), 7.59 (d, J=7.9 Hz, 2H, Ar), 6.91 (d, J=7.9 Hz, 2H, Ar), 2.41–2.56 (m, 4H, benzyl, (6)—CH$_2$—), 1.68–1.75 (m, 2H, 2° aliphatic), 0.95 (s, 9H, t-butyl).

HRMS Calcd. for C$_{22}$H$_{24}$N$_4$O$_4$(M$^+$): 408.1797. Found: 408.1806; other ions at m/e 364, 351, 333, 303, 280, 215, 189, 175, 133, 91, 78, and 69.

Anal. Calcd. for C$_{22}$H$_{24}$N$_4$O$_4$: C, 64.69; H, 5.92; N, 13.72. Found: C, 64.79; H, 5.74; N, 13.80.

EXAMPLE 7

A mixture of 0.19 (1.0 eq) of 4-[2-(2-pivaloylamino-4-hydroxypyrido[2,3-d]pyrimidin-6-yl)-ethyl]benzoic acid 0.19 g (1.5 eq) of phenyl N-phenyl-phosporamidochloridate, 0.24 g (5.0 eq) of N-methylmorpholine, and 20 mL of N-methylpyrrolidone is stirred under nitrogen and at room temperature for one hour and 0.23 g (2.0 eq) of diethyl L-glutamate hydrochloride is added. The mixture is stirred for an additional 24 hours under nitrogen and the solvents then removed by evaporation. Chloroform is added and this mixture is then washed with water, dried over magnesium sulfate, filtered, and concentrated under reduced pressure. The residue is chromatographed, eluting with 2% methanol/chloroform to yield diethyl N-4[2-(2-pivaloylamino-4-hydroxypyrido[2,3-d]pyrimidin-6-yl)ethyl]-benzoyl)-L-glutamate. m.p. >250° C.; $^1$H NMR (CDCl3) delta 8.63 (s, 1H), 8.33 (s, 1H), 7.74 (d, J=8.11 Hz, 2H, Ar), 7.21 (d, J=8.11 Hz, 2H, Ar), 7.19 (d, J=6.9 Hz, 1H, NH), 4.77–4.84 (m, 1H—CH—), 4.24 (q, J=7.4 Hz, 2H, CO$_2$CH$_2$), 4.12 (q, J=7.4 Hz, 2H, COOCH), 3.05 (s, 4H, 2° aliphatic), 1.97–2.61 (m, 4H, 2° aliphatic), 1.34 (s, 9H, t-butyl), 1.29 (t, J=8.4 Hz, 3H, —CH$_3$), 1.22 (t, J=8.4 Hz, 3H, —CH$_3$).

Similarly prepared is diethyl N-(4-[3-(2-pivaloylamino-4-hydroxypyrido[2,3-d]pyrimidin-6-yl)-propyl]benzoyl)-L-glutamate: m.p. >203°–204° C.; $^1$H NMR (CDCl$_3$) delta 8.82 (s, 1H, (7)—H), 8.36 (s, 1H, (5)—H), 7.77 (d, 2H, J=8.31 Hz, Ar), 7.27 (d, 2H, J=8.31 Hz, Ar), 7.06 (d, 1H, J=7.52 Hz, NH), 4.77–4.83 (m, 1H, CH), 4.26 (q, 2H, J=7.34 Hz, CO$_2$CH$_2$), 4.13 (q, 2H, J=7.34 Hz, CO$_2$CH$_2$), 2.73–2.82 (m, 4H, 2° aliphatic), 2.03–2.57 (m, 6H, 2° aliphatic), 1.63 (s, 9H, pivaloyl), 1.32 (t, 3H, J=7.28 Hz, CH$_3$), 1.24 (t, 3H, J=7.28 Hz, CH$_3$).

HRMS calcd. for C$_{29}$H$_{34}$N$_5$O$_7$(M$^+$—CH$_2$CH$_3$): 564.2458 Found: 564.2478.

EXAMPLE 8

A mixture of 0.05 g of diethyl N-(4-[2-(2-pivaloylamino-4-hydroxypyrido[2,3-d]pyrimidin-6-yl)-ethyl]benzoyl-L-glutamate in 20 mL of trifluoroacetic acid is hydrogenated at 50 psi over 0.15 g (3 wt eq) of 5% palladium on charcoal for 24 hours. The reaction mixture is diluted with methylene chloride and filtered and the filtrate concentrated and redissolved in methylene chloride. The organic solution is washed with saturated sodium bicarbonate solution, dried over sodium sulfate, and concentrated. The residue is chromatographed using 4% methanol in methylene chloride to yield diethyl N-(4-[2-(2-pivaloylamino-4-hydroxy-5,6,7,8-tetrahydropyrido[2,3d]pyrimidin-6-yl)ethyl]-benzoyl)-L-glutamate, m.p. >250° C.; IR (KBr) $v_{max}$ 3400, 3280, 2980, 2940, 1735, 1630, 1570, 1460, 1390, 1350, 1310, 1200, 1155, 1025, 930, and 770 cm$^{-1}$; $^1$H NMR (CDCl$_3$) delta 8.56 (brs, 1H, NH), 7.73 (d, J=8.1 Hz, 2H, Ar), 7.23 (d, J=8.1 Hz, 2H, Ar), 7.17 (d, J=7.5 Hz, 1H, NH), 5.15 (brs, 1H, NH), 4.77–4.84 (m, 1H, CHCOO Et), 4.23 (q, J=7.2 Hz, 2H, COOCH$_3$), 4.11 (q, J=7.2 Hz, 2H, COOCH$_3$), 1.61–3.35 (m, 13H, CH, 2° aliphatic), 1.30 (t, J=7.2 Hz, 3H, CH$_3$), 1.29 (s, 9H, t-butyl), 1.22 (t, J=7.2 Hz, 3H, CH$_3$).

Anal. Calcd. for C$_{30}$H$_{37}$N$_5$O$_7$: C, 61.73; H, 7.08 ; N, 12.00. Found: C, 61.49; H, 6.94; N, 12.04.

Similarly prepared in diethyl N-(4-[3-(2-pivaloylamino-4-hydroxy-5,6,7,8-tetrahydropyrido[2,3-d]-pyrimidin-6-yl)propyl]benzoyl)-L-glutamate: m.p. >196°–197° C.; $^1$NMR (CDCl$_3$) delta 8.67 (brs, 1H, NH), 7.73 (d, 2H, J=8.10 Hz, Ar), 7.25 (d, 2H, J=8.10 Hz, Ar), 7.09 (d, 1H, J=7.50 Hz, NH), 4.94 (brs, 1H, NH), 4.80–4.84 (m, 1H, CHCO$_2$Et), 4.25 (q, 2H, J=7.19 Hz, CO$_2$CH$_2$), 4.12 (q, 2H J=7.19 Hz, CO$_2$CH$_2$), 1.71–3.36 (m, 13H, 2° aliphatic, (6)—H), 1.63 (s, 9H, pivaloyl), 1.32 (t, 3H, J=7.16 Hz, CH$_3$), 1.23 (t, 3H, J=7.16 Hz, C$_3$).

HRMS calcd. for C$_{31}$H$_{43}$N$_5$O$_7$(M$^+$): 597.3162. Found: 597.2816.

EXAMPLE 9

A mixture of 0.53 g of diethyl N-(4-[2-(2-pivaloylamino-4-hydroxy-5,6,7,8-tetrahydropyrido[2,3-d]-pyrimidin-6-yl)ethyl]benzoyl)-L-glutamate, 3 mL of 1N sodium hydroxide, and 50 mL of methanol is stirred at room temperature for 70 hours and then acidified with glacial acetic acid and filtered. The solid thus collected is washed with methanol and dried to yield N-(4-[2-(2-amino-4-hydroxy-5,6,7,8tetrahydropyrido-[2,3-d]pyrimidin-6-yl)ethyl]benzoyl)-L-glutamic acid, m.p. >250° C.; $^1$NMR (dTFA) delta 7.85 (d, J=7.9 Hz, 2H, Ar), 7.45 (d, J=9 Hz, 2H, Ar), 5.00–5.25 (m, 1H, CH$_2$COOH), 1.7–3.9 (m, 13H, CH, 2° aliphatic).

Similarly prepared is N-(4-[3-(2-amino-hydroxy-5,6,7,8-tetrahydropyrido[2,3-d]pyrimidin-6-yl) propyl]-benzoyl)-L-glutamic acid: m.p. >250° C.; $^1$H NMR (dTFA, d$^6$DMSO) delta 7.31 (d, 2H, J=8.22 Hz, Ar), 6.93 (d, 2H, J=8.22 Hz, Ar), 4.55–4.61 (m, 1H, CHCO$_2$H), 3.18–3.21 (m, 1H, (6)—H), 2.68 (t, 2H, J=9.55 Hz, benzyl), 1.47–2.48 (m, 8H, 2° aliphatic), 1.31–1.38 (m, 2H, 2° aliphatic), 0.97–1.08 (m, 2H, 2° aliphatic).

What is claimed is:

1. A process for the preparation of a compound of the formula:

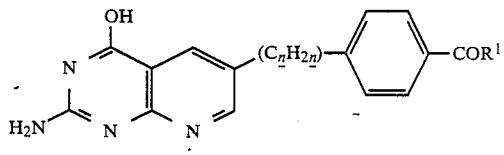

wherein:
R$^1$ is —NHCH(COOR$^2$)CH$_2$CH$_2$COOR$^3$, or OR$^2$ in which each of R$^2$ and R$^3$ is hydrogen or a carboxylic acid protecting group; and
n has a value of from 1 to 3;
which comprises allowing 2,4-diamino-6(1H)-pyrimidinone to react in an inert organic solvent with a compound of the formula:

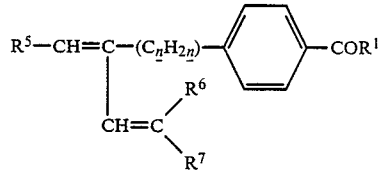

in which R$^1$ and n are as herein defined;
R$^5$ is —OR$^8$ or

each of R$^6$ and R$^7$, independently of the other, is a strong electron withdrawing group; and
each of R$^8$ and R$^9$, independently of the other, is hydrogen or alkyl of 1 to 6 carbon atoms, or R$^8$ and R$^9$, together with the nitrogen atom to which they are attached, are pyrrolidino, morpholino, or piperidino.

2. The process according to claim 1 in which $R^5$ is methoxy or ethoxy.

3. The process according to claim 1 in which $R^5$ is hydroxy.

4. The process according to claim 1 in which each of $R^6$ and $R^7$ is independently selected from the group consisting of cyano, nitro, formyl, carboxy, $S(O)_xR^{10}$, $COR^{10}$, and $COOR^{10}$, in which x is 0, 1 or 2, and each $R^{10}$ is a monovalent inert hydrocarbon group, or when both $R^6$ and $R^7$ are an $R^{10}$-containing group, $R^6$ and $R^7$ together are a single divalent inert hydrocarbon group.

5. The process according to claim 4 wherein each of $R^6$ and $R^7$ is cyano.

6. The process according to claim 1 wherein $R^1$ is $-OR^2$ and $R^2$ is alkyl of 1 to 6 carbon atoms.

7. The process according to claim 1 wherein $R^1$ is $-NHCH(COOR^2)CH_2CH_2COOR^3$ and $R^3$ is alkyl of 1 to 6 carbon atoms.

8. The process according to claim 1 wherein n is 2.

* * * * *